United States Patent [19]
Koch et al.

[11] Patent Number: 5,376,761
[45] Date of Patent: Dec. 27, 1994

[54] IN BED INFANT SCALE

[75] Inventors: Robert J. Koch, Ellicott City; Christopher Dykes, Odenton, both of Md.

[73] Assignee: Chmeda Inc., Liberty Corner, N.J.

[21] Appl. No.: 72,794

[22] Filed: Jun. 4, 1993

[51] Int. Cl.⁵ ............... G01G 19/00; G01G 21/00
[52] U.S. Cl. .................................. 177/145; 177/126
[58] Field of Search ........................ 177/144–146, 177/126

[56] References Cited

U.S. PATENT DOCUMENTS

| | | | |
|---|---|---|---|
| 4,346,771 | 8/1982 | Persson et al. | 177/145 |
| 4,487,276 | 12/1984 | Swersey et al. | 177/126 X |
| 5,065,830 | 11/1991 | Stevenson | 177/126 X |

Primary Examiner—George H. Miller, Jr.
Attorney, Agent, or Firm—Roger M. Rathbun; Larry R. Cassett

[57] ABSTRACT

An in bed infant scale for use with an infant care center and which may be slid underneath the infant platform of the infant care center while the infant is positioned within the center and which causes little disruption to the infant. The infant scale is thus movable from infant care center to infant care center conveniently. The infant scale is easily slid into the infant care center and raises the infant platform on which the infant is positioned such that the infant platform is raised off of its position on its supporting frame and becomes fully supported on the infant scale. Thus the infant scale can weigh the infant platform and the infant resting on that infant platform.

24 Claims, 4 Drawing Sheets

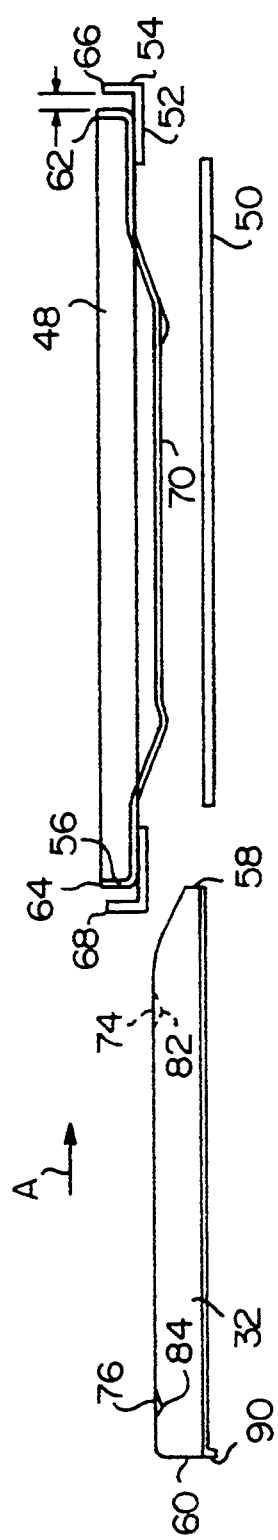
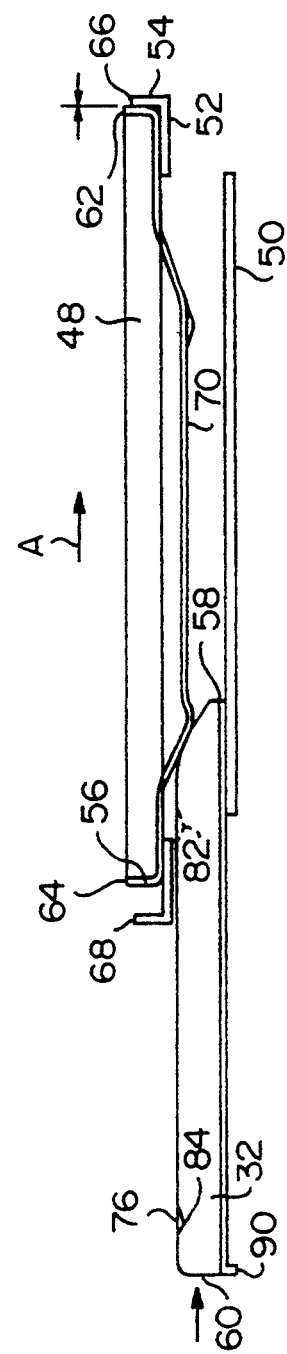
FIG. 2A
FIG. 2B

0
IN BED INFANT SCALE

BACKGROUND OF THE INVENTION

This invention relates to an apparatus and method for weighing an infant and, more particularly, to an apparatus and method of weighing such infant contained in an infant treatment apparatus and where the infant may be weighed with minimal disruption to the infant.

Newborn infants are generally cared for through the use of various types of medical equipment that provide certain functions to assist the infant. For example, premature infants are normally contained for a period of time within an incubator so that they may have a controlled environment to assist in their growth and survival. In other instances, an infant warmer may by used and which comprises of an infant platform on which the infant rests, allowing attention to be given to the infant and which also provides heating to the infant by overhead heaters and/or light radiation for phototherapy.

In either case, it is desirable to have a means of weighing the infant periodically as a indication of its well-being and growth. One of the characteristics desired in carrying out the weighing operation is to maintain the infant as free of disruption as possible and therefore the operation should have a minimum of movement and positioning to the infant. Also, since some of the apparatus that contains and treats the infant is used without the need to weigh the infant, it is desirable that the scale not be permanently built in to the apparatus as the additional cost is not always justifiable if the weighing apparatus is not needed.

Many of the common ways today of weighing infants are disruptive of the infant and require considerable repositioning of the infant. Commonly, one means is to completely remove the infant from the treatment apparatus in order to carry out the weighing procedure. Upon completion of the procedure, the infant is returned to the protected environment. The procedure not only disrupts the infant but removes it from the environment established to protect and support the infant.

In some infant warmers, a scale can be installed beneath the infant, however, the installation requires considerable disruption of the warmer unit. Thus, if an infant is currently in a unit not having such a scale already installed, the infant must be moved to a different unit or maintained somewhere else while the infant support and mattress from the warmer is removed and a cumbersome infant scale inserted into the infant compartment. Upon installation of the scale, the infant support is returned to rest on top of the infant scale and then the infant is replaced in the unit. In addition, in such units, since the infant scale actually is fitted within the infant compartment, the scale must be laboriously cleaned after use with each infant before it can be used with another infant.

In any event, the use of such infant scales requires disruption to the infant since it must be removed from the warm environment and later returned after installing the infant scale. As a further difficulty, since it is expensive to install an infant scale into each warmer unit, it is often necessary to remove the scale from an infant warmer containing an infant to move that scale to another unit where the infant needs to be weighed. Thus, there is disruption to two infants to move the infant scale from unit to unit at a time when disruptions to the infants are undesirable.

Accordingly, the present scales used for weighing infants contained in treatment apparatus are cumbersome and disruptive of the infant as well as inconvenient in use.

SUMMARY OF THE INVENTION

The present invention provides a means and method of weighing an infant with a minimum of disruption to the infant and without removing the infant from its treatment apparatus and without, therefore, interrupting that treatment.

In the present invention, the infant, which is normally lying upon an infant platform within the treatment apparatus, is weighed by sliding the weighing apparatus underneath the infant platform without removal of the infant or, of course, the infant platform on which the infant is positioned. The infant platform is raised off of its normal resting base such that it becomes supported entirely by the weighing apparatus so that the apparatus can read the weight of the infant platform and everything resting upon that platform, including the infant. If the weight of the platform is known from previous readings, the weight of the infant may be determined directly, otherwise, the infant may be momentarily raised by the attending personnel off of the platform and a reading taken of the weight of the platform and all items resting thereof. Then the infant is then replaced, its weight is readily taken.

Thus, there is very little disruption to the infant and yet an accurate reading of the infant weight is ascertainable. In addition, in the preferred embodiment, the scale is of a standard size with respect to the infant apparatus and therefore may be removed from one apparatus and moved to another for weighing of another infant. Therefore, for example, one nursery having a large number of infant warmers need not have a scale for each of the warmers since the scale may be moved from warmer to warmer easily and conveniently without disruption to any of the infants and used at each location to weigh the particular infant.

Additionally, since the scale apparatus does not actually enter the infant compartment or come in contact with the infant, it need not be cleaned after each use but may be continually used with further infants.

BRIEF DESCRIPTION OF THE DRAWINGS

FIGS. 2A-2F are schematic views showing the progression of an infant scale being slid into position in an infant care apparatus;

DESCRIPTION OF THE PREFERRED EMBODIMENT

Figure 1:
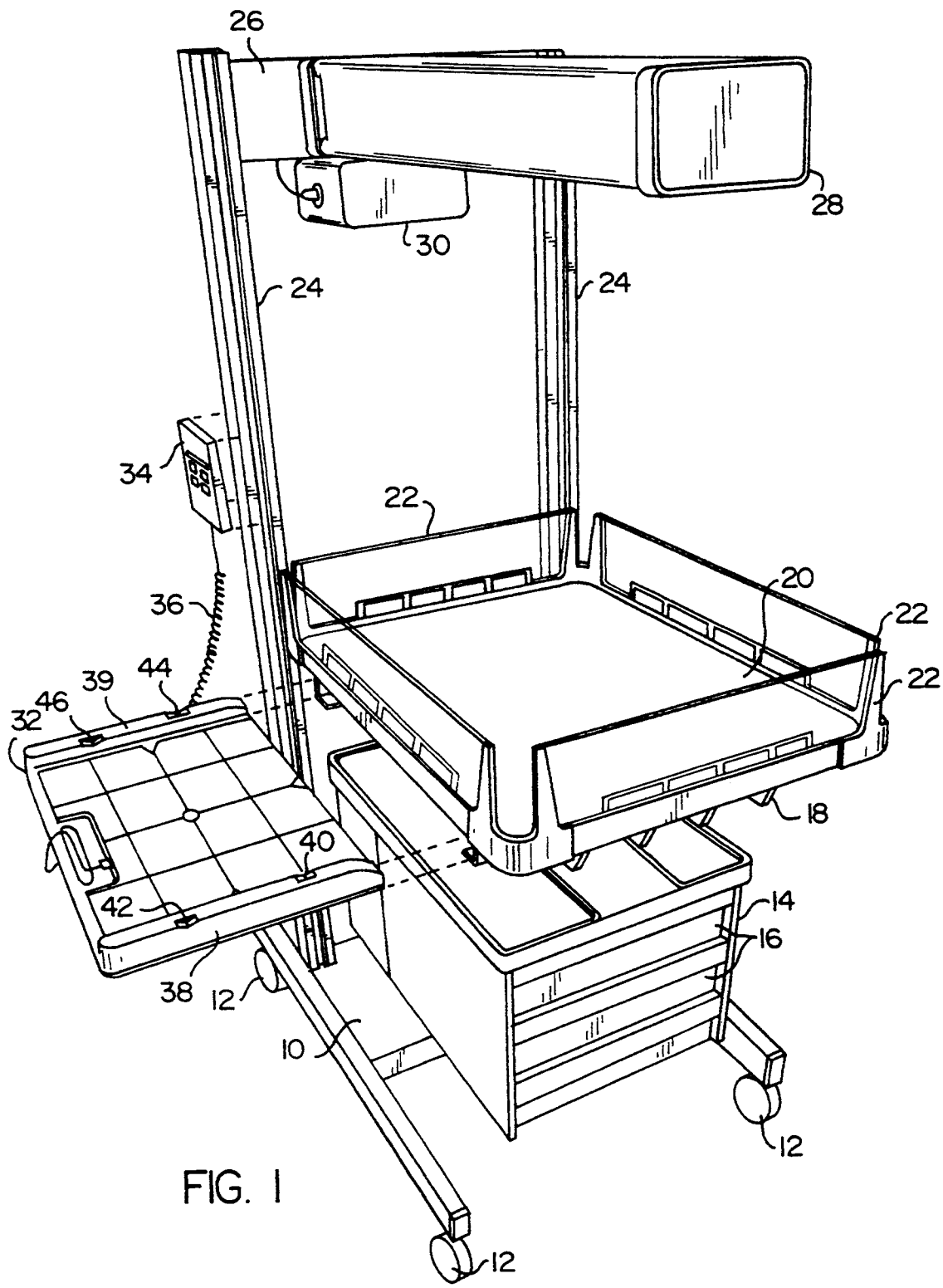
FIG. 1 is an isometric view of an infant care center having an in bed infant scale readied for insertion into the infant care center and constructed in accordance with the present invention.

Referring now to FIG. 1, there is shown an isometric view of an infant care center having an in bed scale constructed in accordance with the present invention and positioned to be inserted into the infant care center to carry out the weighing of an infant. As used, herein, the term infant care center will be used for convenience, it being understood that the invention can be used with a variety of apparatus used for infant care, including incubators, infant warmer systems, bassinets as well as other like equipment.

As shown, the infant care center includes a frame 10 having wheels 12 so that the infant care center is easily movable. A cabinet 14 rests upon the frame 10 and may include one or more drawers 16 for containing items used in attending to an infant.

The frame 10 includes an infant pedestal 18 mounted atop of the cabinet 14 and on which is located an infant mattress 20 which underlies an infant positioned for treatment. An infant platform (not shown in FIG. 1) rests upon frame 10 and underlies and supports the infant mattress 20 and will be later explained. As noted, the upper surface of the infant mattress 20 is generally planar and is pliable for the comfort of the infant and further may be surrounded by guards 22, generally of clear plastic material, and which contain the infant upon the upper surface of the infant mattress 20. Generally, the guards 22 are releasable and/or removable for complete access to the infant.

Frame 10 may include vertical struts 24 which project upwardly ending in a horizontal cross member 26 on which may be mounted a heater 28 which extends outwardly from the horizontal cross member 26 and contains heater elements (not shown) for projecting radiant heat downwardly to heat the infant lying upon the infant mattress 20. A control module 30 may be mounted on the horizontal cross member 26 and which contains the various electrical control s to operate the infant care center.

A weighing means or infant scale 32 is shown and is in position to be inserted into the infant care center. A scale controller 34 is preferably mounted remote to the infant scale 32 and may contain the electrical components such as a readout so that the attendant can easily and conveniently see the weight of the infant. A suitable electrical cable 36 connects the scale controller 34 to the infant scale 32. As will become apparent, the scale controller 34 may be permanently attached to various infant care centers in a nursery, or may be transportable along with the infant scale and be moved from infant care center to infant care center to obtain the weight of different infants.

The infant scale 32 also includes upstanding side flanges 38, 39 of a predetermined height, the purpose of which will later be explained. A plurality of female detents 40, 42, 44 and 46 are also provided and are formed on the upper surface of each of the upstanding side flanges 38, 39 and, again, the purpose of such detents will later become apparent.

Figure 2C:
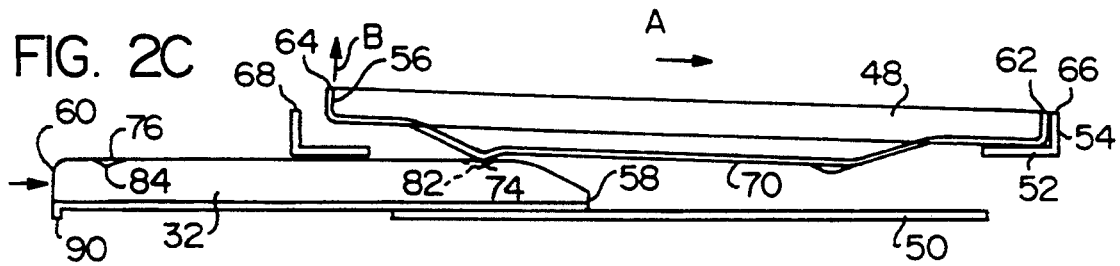

Turning now to FIGS. 2A–2F, there is shown a sequence of schematic views of an infant scale 32 being slid underneath the infant platform 48 in a series of progressive steps. In FIG. 2A, the infant scale 32 is in position for insertion into the infant care center and is to be inserted in the direction of the arrow A. In the FIGS. 2A–2F, the frame 10 includes a lower support 50 on which the infant scale 32 ultimately rests and an upper support 52 that underlies the infant platform and which provides support for infant platform 48. The dimension of the separation between the lower surface of the upper support 52 and the upper surface of the lower support 52 is designed to receive the infant scale 32 and is standard on the various apparatus for treating the infant. In this way, a standard infant scale 32 may be inserted into various infant care centers and moved readily from one infant care center to another infant care center for use therein.

As such, the upper support 52 generally provides the support through its position underneath the infant platform and which further includes a continuous raised edge 54 that surrounds the periphery of the infant platform 48. In the preferred embodiment, the infant platform 48 is rectangular and therefore the upper support 52 includes a continuous raised edge 54 having four sides paralleling and surrounding adjacent sides of the infant platform 48.

The infant platform 48 also has a raised lip 56 that surrounds its periphery and which serves as a retainer for liquids and/or objects on the infant platform 48, preventing spillage to portions of the infant care center beneath the infant platform 48. Again, in the preferred embodiment, since the infant platform 48 is rectangular, there are four sides of the infant platform 48 having the raised lip 56 surrounded, as explained, by corresponding edges of the continuous raised edge 54 of upper support 52.

For purposes of reference to the features disclosed in FIGS. 2A–2F, the edge of the infant scale 32 that is initially inserted into the infant care center when slid underneath the infant platform 48 in the direction shown by arrow A. will be referred to as the distal edge 58 and the opposite edge as the proximal edge 60.

Again, for point of reference, the side of the infant platform 48 toward which the infant scale 32 moves during insertion will be referred to as the far side 62 and the opposite side referred to as the near side 64. Taking the same direction of insertion, that is, in the direction of the arrow A, the side of the upper support 52 toward which the infant scale 32 is slid is referred to as the far side 66 of upper support 52 and the opposite side referred to as the near side 68 of upper support 52. It should be noted, however, that with respect to the infant scale 32, the proximal and distal edges, 60 and 58, respectively, are the same on each scale used in accordance with the present invention, however, the direction of the far and near sides 62 and 64 of infant platform 48 and the far and near sides 66 and 68 of the upper support 52 may change since the infant scale 32 can, in the preferred embodiment, be slid beneath the infant platform 48 from more that one direction.

Figure 2D:
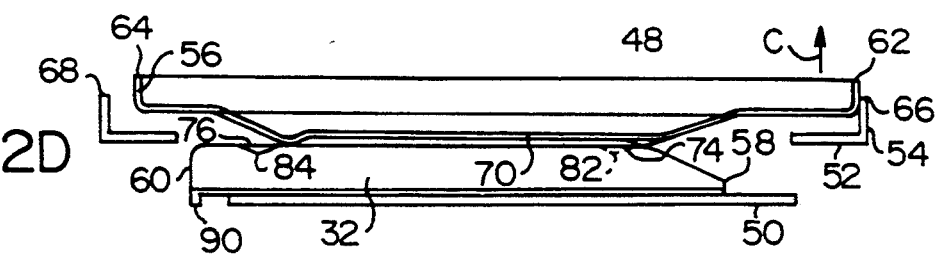
Figure 2E:
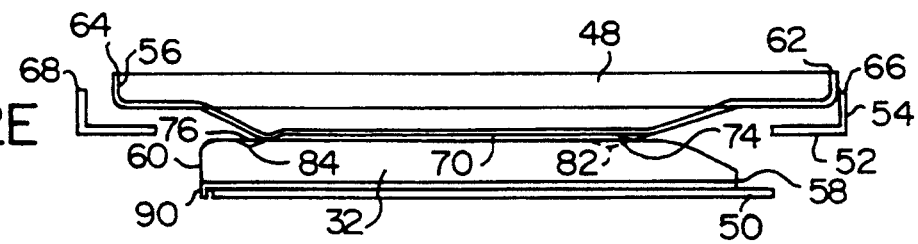
Figure 2F:
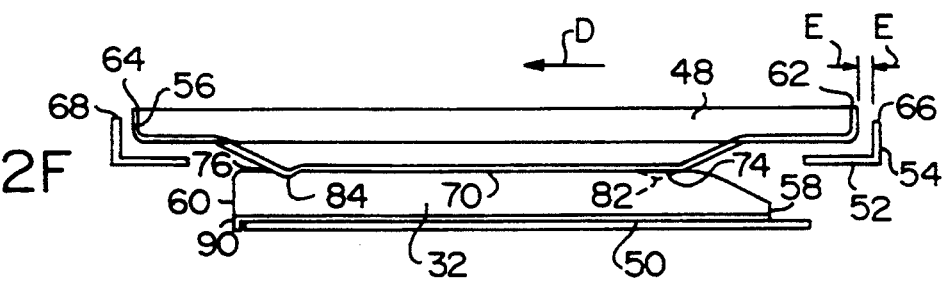
Figure 3:
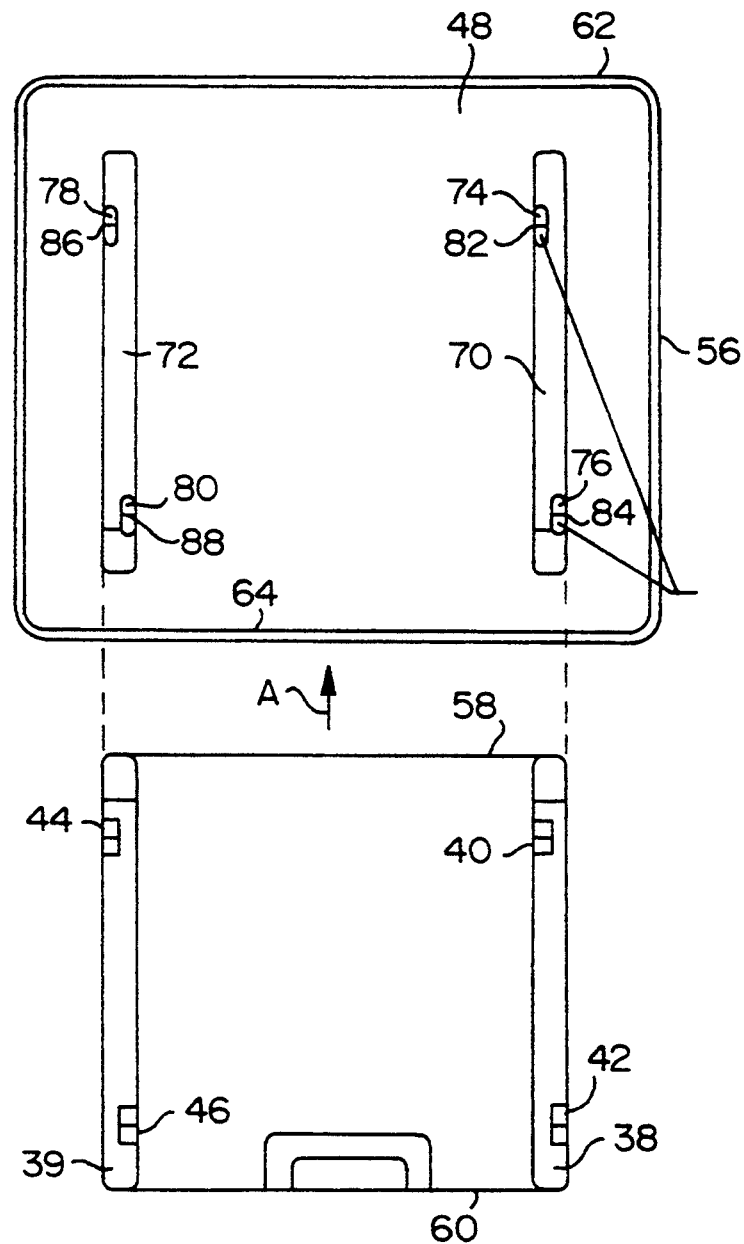
FIG. 3 is a plan view of an infant platform and infant scale used accordance with the present invention.

Taking FIG. 3 in connection with FIGS. 2A–2F, downwardly inclined planes 70 and 72 are formed in the lower surface of the infant platform 48 and which align with the upper side flanges 38, 39 of the infant scale 32 when the same is slid into the infant care center. In the preferred form, two downwardly inclined planes are utilized on the infant platform and two upstanding flanges are located on the infant scale 32, however, a various number of such corresponding flanges and inclined planes may be used. Male detents 74, 76, 78, and 80 are formed on the downwardly inclined planes 70 and 72 and have apexes 82, 84, 86 and 88 as will be explained. In FIG. 3, it will be noted that the male detents 74 and 76 are offset with respect to each other on the same downwardly inclined plane 70 as are male detents 78 and 80 on downwardly inclined plane 72 such that male detents formed on the same downwardly inclined plane are not in alignment.

Similarly, the alignment of the female detents 40, 42, 44 and 46 are also misaligned, in particular, the female detents 40 and 42 formed on the same upstanding flange 38 are offset as are the female detents 44 and 46 on the other of the upstanding flanges 39.

Taking FIG. 2B, the infant scale 32 has been progressively slid in the direction of the arrow A beneath the infant platform 48. At the position of FIG. 2B, the distal edge 58 of the infant scale 32 has encountered the downwardly inclined planes 70 and 72 and the effect is to push the entire infant platform 48 in the direction of arrow A such that the far side 62 of the infant platform 48 abuts against the far side of the upper support 52.

In FIG. 2C, the infant scale 32 has been slid further in the direction of arrow A and the near side 64 of the infant platform 48 is raised upwardly in the direction of the arrow B as the infant scale 32 pushes upwardly against the downwardly inclined planes 70 and 72. In this position, the mating detents, made up of the female detents 40 and 44 and the male detents 76 and 80 are adjacent each other, however, due to the offset or misalignment, the respective male and female detents do not engage with each other (note the FIG. 3 misalignment between the mating detents).

In FIG. 2D, the infant scale 32 is almost fully slid beneath the infant platform 48 and, as noted, the far side 62 of the infant platform 48 now moves upwardly in the direction of the arrow C such that the entire infant platform 48 now rides completely upon the infant scale 32 and is relatively level with respect to the upper and lower supports 52 and 50 of frame 10.

In FIG. 2E, the infant scale 32 has been fully slid beneath the infant platform 48 and a stop 90 formed on the infant scale 32 engages the lower support 52 and prevents the infant scale 32 from being moved further forward into the infant care center. The position of the stop 90 is designed to be precise so that the infant scale 32, when inserted to its fullest, occupies a precise position with respect to the infant platform 48.

Finally, in FIG. 2F, the infant platform 48 has settled into its desired position supported entirely by the infant scale 32. To reach the position of FIG. 2F, it should be noted that the apexes 82–88 formed at the lowermost part of the male detents 74–80 did not, in FIG. 2E, position themselves fully within the female detent 40–46. The apexes 82–88 were partially entering the female detents 40–46 but were prevented from bottoming out in the female detents by the forward position of the infant platform 48. In essence, the stop 90 positions the infant scale 32 slightly short of the ultimate gravitational position where the infant platform 48 would position itself upon the infant scale 32 and mating male and female detents are not completely aligned.

To reach the position of FIG. 2F, the infant platform 48 slides backwardly, seating the apexes 82–88 within female detents 40–46 as the force of gravity pulls the infant support downwardly as the downwardly inclined planes 70 and 72 slide into the female detents 40–46 moving the infant platform 48 in the direction of arrow D so that the male and female detents fit together. Thus, in sliding backwardly, the far side 62 of infant platform 48 moves away from the far side 66 of upper support 52 such that the corresponding far edges of the components are no longer in abutment and a gap is created as shown by the arrows E—E. Thus, there is no interference between the far edges of the infant platform 48 and the upper support 52. The infant platform 48 is thus positioned properly and all of the four sides are clear of obstruction or frictional engagement with the upper support 52 and the infant may be weighed.

While the above presents a working embodiment of the invention, there are others which will be obvious to those skilled in the art. The invention is not to be limited to the embodiments specifically described but is to be interpreted only in conjunction with the scope of the appended claims and their functional equivalents.

We claim:

1. An infant care apparatus comprising a frame, an infant platform resting upon said frame and adapted to underlie an infant, weighing means dimensioned to be slid underneath said infant platform, means to remove said infant platform from resting on said frame such that said infant platform is fully supported by said weighing means, said weighing means thereby ascertaining the weight of the infant platform and objects resting upon said infant platform including the infant.

2. An infant care apparatus as defined in claim 1 wherein said means to remove said infant platform from resting on said frame comprises means to raise said infant platform from said frame.

3. An infant care apparatus as defined in claim 2 wherein said means to raise said infant platform comprises positioning said weighing means beneath said infant platform.

4. An infant care apparatus as defined in claim 2 wherein said weighing means is a scale and said means to raise said infant platform is caused by the thickness of said scale.

5. An infant care apparatus as defined in claim 2 wherein said infant care apparatus is an infant warmer.

6. A method of weighing an infant resting upon an infant platform, supported upon a frame, said method comprising;
(a) sliding an infant scale underneath the infant platform to remove the infant platform from its position upon the frame,
(b) supporting the infant platform wholly upon the infant scale,
(c) ascertaining the weight of the infant from the infant scale.

7. A method of weighing an infant as described in claim 6 wherein the step of removing the infant platform from the frame comprises the step of moving the infant platform upwardly by insertion of the infant scale.

8. An infant warmer having means to provide heat to a newborn infant, said infant warmer comprising a base, an infant support resting upon said base and adapted to underlie an infant, an infant scale adapted to be slid underneath said infant support, said infant scale being dimensioned to cause said infant support to be elevated off of said base and rest entirely upon said scale when slid underneath said infant support, whereby said scale can measure the weight of the infant support and objects resting upon said infant support including the infant.

9. An infant warmer as defined in claim 8 wherein said infant scale comprises a plurality of load cells and further comprises a display means to display the scale readings of weight.

10. An infant warmer as defined in claim 9 wherein said display means comprises an electronic readout device located remote from said infant scale positioned beneath said infant support.

11. An infant care apparatus for holding and providing heat to an infant, said infant care apparatus having a frame and having an infant support having lateral edges and supported upon said frame, said frame having at least one lateral edge adjacent to and parallel to a lateral edge of said infant support, a scale adapted to be slid underneath said infant support in a direction toward said at least one lateral edge of said frame to raise the infant support with respect to said frame and causing said lateral edge of said infant support to abut against said at least one lateral edge of said frame, and means to move said infant support a slight distance in a direction away from said lateral edge of said frame to create a clearance between said lateral edge of said infant support and said at least one lateral edge of said frame to allow free movement therebetween.

12. An infant care apparatus as defined in claim 11 wherein said means to move said infant support a slight distance in a direction away from said lateral edge of said frame comprises at least one detent formed in said scale and at least one detent formed in said infant support, said at least one detents positioned to interengage each other to seat said infant support in a predetermined position with respect to said scale.

13. An infant care apparatus as defined in claim 11 wherein said at least one detent in said infant support and said at least one detent in said scale comprise, respectively, at least one male detent and at least one female detent.

14. An infant care apparatus as defined in claim 13 wherein said at least one male detent and said at least one female detent comprise a plurality of detents.

15. An infant care apparatus as defined in claim 14 wherein said plurality of male detents each comprise downwardly directed inclined planes, each having an apex adapted to settle within each of the female detents.

16. An infant care apparatus as defined in claim 15 wherein said movement of said infant support in a direction away from said lateral edge of said frame is caused by the settlement of said male detents into said female detents.

17. An infant care apparatus for containing an infant, said infant care apparatus having a frame and having an infant platform having a peripheral raised lip supported upon said frame, said frame having a peripheral raised edge adjacent to and surrounding said peripheral raised lip of said infant platform, said infant platform having at least one downwardly inclined plane, a scale adapted to be slid underneath said infant platform thereby moving said infant platform in a first direction and causing a portion of said peripheral raised lip of said infant platform to abut against a portion of said peripheral raised edge of said frame, said scale having at least one upstanding flange that aligns with said at least one downwardly inclined plane of said infant platform to raise said infant platform off from said frame, said at least one upstanding flange having a detent and said at least one downwardly inclined plane having a detent, said at least one detents adapted to engage each other and cause said infant platform to move in a direction opposite to said first direction to disengage said abutting portions of said peripheral raised lip of said infant platform and said peripheral raised edge of said frame and to support said infant platform in a predetermined fixed position fully supported upon said scale such that said infant platform can freely move with respect to said frame for weighing said infant platform by said scale.

18. An infant care apparatus as defined in claim 17 wherein said peripheral raised lip of said infant platform and said peripheral raised edge of said frame are rectangular and said abutting portions are each one side of a rectangle.

19. An infant care apparatus as defined in claim 17 wherein said detent on said downwardly inclined plane comprises a male detent having an apex that seats within said detent of said at least one upstanding flange.

20. An infant care apparatus as defined in claim 19 wherein said detent on said at least one upstanding flange comprises a female detent.

21. An infant care apparatus as defined in claim 20 wherein said at least one upstanding flange has at least two female detents, said female detents being misaligned with respect to each other along said at least one upstanding flange.

22. An infant care apparatus as defined in claim 21 wherein said at least one downwardly inclined plane has at least two male detents misaligned with respect to each other along said at least one downwardly inclined flange and said male detents of said at least one downwardly inclined plane and said two female detents of said at least one upstanding flange mutually engage each other only in one position of said scale and said infant platform.

23. An infant care apparatus as defined in claim 22 wherein said at least one downwardly inclined plane comprises two downwardly inclined planes and said at least one upstanding flange comprises two upstanding flanges.

24. An infant care apparatus as defined in claim 23 wherein said apparatus is an infant warmer.

* * * * *